United States Patent [19]

Bayer et al.

[11] 4,445,930

[45] May 1, 1984

[54] HERBICIDAL 4-TRIFLUOROMETHYL-4-NITRODIPHENYL ETHERS

[75] Inventors: Horst O. Bayer, Levittown; Colin Swithenbank, Perkasie; Roy Y. Yih, Doylestown, all of Pa.

[73] Assignee: Rohm and Haas Company, Philadelphia, Pa.

[21] Appl. No.: 302,921

[22] Filed: Sep. 16, 1981

Related U.S. Application Data

[60] Division of Ser. No. 939,086, Sep. 1, 1978, which is a division of Ser. No. 808,415, Jun. 20, 1977, Pat. No. 4,185,995, which is a division of Ser. No. 617,562, Sep. 29, 1975, Pat. No. 4,046,798, which is a division of Ser. No. 331,719, Feb. 12, 1983, Pat. No. 3,928,416, which is a continuation-in-part of Ser. No. 234,651, Mar. 14, 1982, Pat. No. 3,798,276.

[51] Int. Cl.³ .......... A01N 9/20

[52] U.S. Cl. .......... 71/105

[58] Field of Search .......... 71/105; 560/21; 260/465 D, 465 F

[56] References Cited

U.S. PATENT DOCUMENTS

| | | | |
|---|---|---|---|
| 3,154,398 | 10/1964 | McRae | 560/21 |
| 3,322,528 | 5/1967 | Martin | 560/21 |
| 3,652,645 | 3/1972 | Theissen | 560/21 |
| 4,039,588 | 8/1977 | Wilson | 560/21 |

*Primary Examiner*—Paul J. Killos

*Attorney, Agent, or Firm*—Polly E. Ramstad; William E. Lambert, III

[57] ABSTRACT

Compounds of the formula

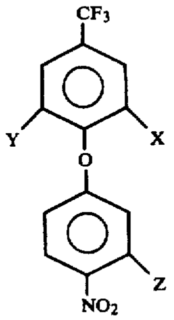

wherein

X is a hydrogen atom, a halogen atom, a trihalomethyl group, an alkyl group, or a cyano group, Y is a hydrogen atom, a halogen atom, or a trihalomethyl group, and Z is a hydroxy group, an alkoxy group, and alkyl group, a halogen atom, an amino group, an alkylthio group, a cyano group, a carboxy group, a carbalkoxy group, a carboxyalkyl group, an carbalkoxyalkyl group, an alkanoyloxy group, or a carbamoyloxy group, and compositions containing these compounds exhibit herbicidal activity.

12 Claims, No Drawings

HERBICIDAL 4-TRIFLUOROMETHYL-4-NITRODIPHENYL ETHERS

CROSS REFERENCE TO RELATED APPLICATIONS

This is a divisional of application Ser. No. 939,086 filed Sept. 1, 1978 which is a divisional of application Ser. No. 808,415 filed June 20, 1977 now U.S. Pat. No. 4,185,995, which is a division of Ser. No. 617,562 filed Sept. 29, 1975 now U.S. Pat. No. 4,046,798, which is a division of application Ser. No. 331,719 filed Feb. 12, 1973 now U.S. Pat. No. 3,928,416, which is a continuation-in-part of application Ser. No. 234,651 filed Mar. 14, 1972 now U.S. Pat. No. 3,798,276.

This case is related to application Ser. No. 111,560 filed Jan. 14, 1980 now U.S. Pat. No. 4,330,324, which is a divisional of application Ser. No. 881,227 filed Feb. 27, 1978 now U.S. Pat. No. 4,220,468, which is a division of application Ser. No. 719,484 filed Aug. 31, 1976 now U.S. Pat. No. 4,093,446, which is a continuation-in-part of application Ser. No. 617,560 filed Sept. 29, 1975 now U.S. Pat. No. 4,063,929 which is a continuation-in-part application of Ser. No. 331,719 filed Feb. 12, 1973 (referred to above) and application Ser. No. 719,484 now U.S. Pat. No. 4,093,446 is also a continuation-in-part of application Ser. No. 617,560 filed Sept. 29, 1975 now U.S. Pat. No. 4,046,798. This case is also related to application Ser. No. 216,335 filed Dec. 15, 1980, which is a continuation-in-part of application Ser. No. 926,355 filed July 20, 1978, which in turn is a continuation-in-part of application Ser. No. 808,415 filed June 20, 1977 now U.S. Pat. No. 4,185,995. This case is also related to application Ser. No. 939,291 filed Sept. 1, 1978 which is an application for reissue of U.S. Pat. No. 3,928,416 and application Ser. No. 939,292 filed Sept. 1, 1978 which is an application for reissue of U.S. Pat. No. 4,063,929.

This invention relates to novel compounds which show activity as herbicides, to novel herbicidal compositions which contain these compounds, and to new methods of controlling weeds with these herbicidal compositions.

Certain ethers have been shown to be effective weed control agents. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition. Furthermore, the diphenyl ethers heretofore disclosed as herbicides are not completely effective. An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise be dissipated so as not to poison the soil permanently. The known diphenyl ether herbicides fall short of these ideals, and it would thus be desirable to have new herbicides which show even more selective control of undesirable plants among desirable crop plants or which complement the known diphenyl ethers in activity.

In accordance with the present invention, there is provided a new class of novel diphenyl ethers having the formula

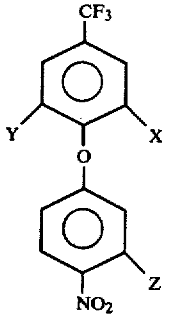

(I)

wherein

- X is a hydrogen atom, a halogen atom, preferably a fluorine atom or a chlorine atom, a trihalomethyl group, preferably a trifluoromethyl group, a $(C_1-C_4)$alkyl group, preferably a methyl group, or a cyano group,
- Y is a hydrogen atom, a halogen atom, preferably a fluorine atom or a chlorine atom, or a trihalomethyl group, preferably a trifluoromethyl group, and
- Z is a hydroxy group, an alkoxy group, preferably having 1 to 6 carbon atoms, and most preferably 1 to 4 carbon atoms, an alkyl group, preferably having 1 to 4 carbon atoms, a halogen atom, preferably a chlorine atom or a fluorine atom, an amino group, preferably having up to 6 carbon atoms, an alkylthio group, preferably having 1 to 4 carbon atoms, a cyano group, a carboxy group, a carbalkoxy group, $-CO_2R$, preferably having 1 to 4 carbon atoms in the alkoxy moiety, a carboxyalkyl group, $-R'\lambda CO_2H$, preferably having up to 4 carbon atoms, a carbalkoxyalkyl group, $-R'CO_2R$, preferably having up to 6 carbon atoms, an alkanoyloxy group, $-OCOR$, preferably having up to 4 carbon atoms, optionally substituted with a halogen atom, or a carbamoyloxy group, $-OCONH_2$, $-OCONHR$, or $-OCONR_2$, preferably having up to 6 carbon atoms.

In the above definitions of the Z substituent, R represents an alkyl group, and R' represents a divalent alkylene group. The alkyl or alkylene portion of the alkyl-containing X and Z substituents can have either a straight- or branched-chain or a cyclic spatial configuration.

As used in the present specification and claims, the term "alkoxy group" is intended to include both unsubstituted alkoxy groups as well as substituted alkoxy groups which have one or more of the hydrogen atoms replaced by a substituent group. Among the substituted alkoxy groups which Z can represent are alkoxy groups of preferably up to 4 carbon atoms substituted with a halogen atom, a hydroxy group, a $(C_1-C_4)$ alkoxy group, a carboxy group, a carbalkoxy group, preferably having up to 4 carbon atoms in the ester alkoxy group, a trihaloalkyl group, preferably a trifluoromethyl group, an alkenyl group, an alkynyl group, preferably an ethynyl group, an amino group, an alkyl- or dialkylamino group, including heterocyclic substituents such as morpholino, piperazino, piperidino, and the like, and preferably having a total of up to 4 carbon atoms, an alkylthio group, preferably having up to 4 carbon atoms, a alkylsulfonyl group, preferably having up to 4 carbon atoms, an epoxy group, an alkylcarbonyl group, including halo-substituted alkylcarbonyl, and preferably having up to 4 carbon atoms in the alkyl group, most preferably methylcarbonyl, a carbamoyl group, including alkyl- or dialkylcarbamoyl, preferably having a total of up to 4 carbon atoms in the alkyl substituents.

The term "amino group" as used in the present specification and claims is intended to include an unsubstituted amino group, $-NH_2$, as well as amino groups having one or both hydrogen atoms replaced by substituent groups. Among the substituted amino groups which Z can represent are amino groups substituted with one or two alkyl groups, preferably having a total of up to 6 carbon atoms, halo-, hydroxy-, or alkoxy-substituted alkyl groups, preferably having a total of up to 6 carbon atoms, one or two alkylthio carbonyl groups, preferably having a total of up to 4 carbon atoms in the alkyl moiety, carboxy groups, carbalkoxy groups, preferably having up to 4 carbon atoms in the alkoxy group, carbamoyl groups, including alkyl or dialkylcarbamoyl groups, preferably having up to 4 carbon atoms in the alkyl moiety, alkylcarbonyl groups, preferably having up to 4 carbon atoms, or halo-substituted alkylcarbonyl groups, preferably having up to 4 carbon atoms.

The substituted amino groups can also be heterocyclic amino groups, such as piperidino, piperazino, morpholino, pyrrolidinyl, and the like. When the Z substituent is or contains a carboxy group, either the free acid or the salt form can be used.

When Z is an alkyl group, it may be optionally substituted with a hydroxy group, a $(C_1-C_4)$alkoxy group, or a halogen atom, preferably a chlorine atom.

These novel compounds have been found to show unexpected activity as weed control agents. In a preferred embodiment of the invention, X is a halogen atoms or a cyano group, Y is a hydrogen atom or a halogen atom, and Z is an alkoxy group.

Examples of the compounds of the invention embraced by Formula I include:

2-chloro-α,α,α-trifluoro-p-tolyl-4-nitro-m-tolyl ether,
2-bromo-α,α,α-trifluoro-p-tolyl-3-butyl-4-nitrophenyl ether,
2,α,α,α-tetrafluoro-p-tolyl-4-nitro-3-n-propoxyphenyl ether,
2-chloro-6,α,α,α-tetrafluoro-p-tolyl-3-methylthio-4-nitrophenyl ether,
2-chloro-α,α,α-trifluoro-p-tolyl-3-propyl-4-nitrophenyl ether,
2-chloro-α,α,α-trifluoro-p-tolyl-3-ethoxy-4-nitrodiphenyl ether,
α,α,α-trifluoro-2-iodo-p-tolyl-3-ethoxy-4-nitrophenyl ether,
2,6-dichloro-α,α,α-trifluoro-p-tolyl-4-nitro-3-n-propoxyphenyl ether,
α,α,α,α′,α′,α′-hexafluoro-2,4-xylyl-3-n-butoxy-4-nitrophenyl ether,
2-cyano-α,α,α-trifluoro-p-tolyl-3-ethoxy-4-nitrophenyl ether,
2-chloro-6-cyano-α,α,α-trifluoro-p-tolyl-4-nitro-3-n-propoxyphenyl ether,
2-cyano-α,α,α-trifluoro-p-tolyl-3-carboxy-4-nitrophenyl ether,
2,6-dibromo-α,α,α-trifluoro-p-tolyl-3-methoxymethoxy-4-nitrophenyl ether,
2-chloro-α,α,α-trifluoro-p-tolyl-3-(2-hydroxyethoxy)-4-nitrophenyl ether,
2-α,α,α-tetrafluoro-p-tolyl-4-nitro-3-n-propylaminophenyl ether,
2-chloro-α,α,α-trifluoro-p-tolyl-3-dimethylamino-4-nitrophenyl ether,
2-cyano-α,α,α-trifluoro-p-tolyl-3-carbethoxy-4-nitrophenyl ether,
2,6-dichloro-α,α,α-trifluoro-p-tolyl-3-carbethoxy-4-nitrophenyl ether,
2-ethyl-α,α,α-trifluoro-p-tolyl-3-(2-carboxy ethoxy)-4-nitrophenyl ether, α,α,α′,α′-hexafluoro-2,4-xylyl-3-carbethoxymethyl-4-nitrophenyl ether, 2-cyano-α,α,α-trifluoro-p-tolyl-3-(2-carboxy propyl)-4-nitrophenyl ether,
2,α,α,α-tetrafluoro-p-tolyl-3-carbethoxymethyl-4-nitrophenyl ether,
2-chloro-α,α,α-trifluoro-p-tolyl-3-(3,3-diethylureido)-4-nitrophenyl ether, 2-chloro-6-cyano-α,α,α-trifluoro-p-3-acetamido-4-nitrophenyl ether,
2-chloro-α,α,α-trifluoro-p-tolyl-3-carbethoxyamino-4-nitrophenyl ether,
2-chloro-α,α,α-trifluoro,-p-tolyl-3-chloro-4-nitrophenyl ether,
2-chloro-α,α,α-trifluoro-p-tolyl-3-hydroxy-4-nitrophenyl ether,
2-bromo-α,α,α-trifluoro-p-tolyl-3-butynyloxy-4-nitrophenyl ether,
2-cyano-α,α,α-trifluoro-p-tolyl-3-(2-methyl)-propynyloxy-4-nitrophenyl ether,
2,6-dichloro-α,α,α-trifluoro-p-tolyl-3-(2,2,2-trifluoro)-ethoxy-4-nitrophenyl ether,
2-chloro-α,α,α-trifluoro-p-tolyl-3-(2-dimethylaminoethoxy)-4-nitrophenyl ether,
2-bromo-α,α,α-trifluoro-p-tolyl-3-acetoxy-4-nitrophenyl ether,
α,α,α,α′,α′,α′-hexafluoro-2,4-xylyl-3-(2-hydroxyethylamino)-4-nitrophenyl ether
$\alpha^4,\alpha^4,\alpha^4$-trifluoro-2,4-xylyl-3-amino-4-nitrophenyl ether,
2-chloro-α,α,α-trifluoro-p-tolyl-3-morpholino-4-nitrophenyl ether,
2-cyano-α,α,α-trifluoro-p-tolyl-3-(N-methylcarbamoyloxy)-4-nitrophenyl ether,
2-chloro-6,α,α,α-tetrafluoro-p-tolyl-3-propionamido-4-nitrophenyl ether,
2-chloro-α,α,α-trifluoro-p-tolyl-3-chloroacetamido-4-nitrophenyl ether,
$\alpha^4,\alpha^4\alpha^4$-trifluoro-2,4-xylyl-3-(2,3-epoxypropoxy)-4-nitrophenyl ether,
2-chloro-α,α,α-trifluoro-p-tolyl-3-(2,3-dihydroxypropoxy)-4-nitrophenyl ether,
2-cyano-α,α,α-trifluoro-p-tolyl-3-(2-methylthioethoxy)-4-nitrophenyl ether,
2-chloro-α,α,α-trifluoro-p-tolyl-3-(1-ethyl-3-methylureido)-4-nitrophenyl ether,
2-bromo-α,α,α-trifluoro-p-tolyl-3-(2-methylsulfonylethoxy)-4-nitrophenyl ether,
α,α,α,α′,α′,α′-hexafluoro-2,4-xylyl-3-(3-methylureido)-4-nitrophenyl ether, 2-cyano-α,α,α-trifluoro-p-tolyl-3-ethylthiocarbonylamido-4-nitrophenyl ether,
2-cyano-α,α,α-trifluoro-p-tolyl-3-cyano-4-nitrophenyl ether,
2,6-dichloro-α,α,α-trifluoro-p-tolyl-3-carboxy-4-nitrophenyl ether,
2-chloro-α,αα-trifluoro-p-tolyl-3-(1-carbamoylethoxy)-4-nitrophenyl ether, 2-bromo-α,α,α-trifluoro-p-tolyl-3-(3-oxobutoxy)-4-nitrophenyl ether, and the like.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Post-emergence herbicides are those which are applied after the plants have emerged and during their growth period.

Among the crops on which the diphenyl esters of the invention can be advantageously employed are, for example, cotton, soybeans, peanuts, safflower, beans, peas, carrots, corn, wheat, and other cereal crops.

Diphenyl ethers of the invention are useful for controlling weeds in rice plants. When used in transplanted rice crops, the ethers can be applied either preemergence or post-emergence to the weeds—that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12, and most preferably about 0.25 to 4, pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsions concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual".

The diphenyl ether compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25 to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similary to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10 to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20 to 98%, preferably about 40 to 75%. A dispersing agent can constitute about 0.5 to about 3% of the composition, and a wetting agent can constitute from about 0.1 to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20 to 80% of the active ingredient are commonly made and are subsequently diluted to about 1 to 10% use concentration.

Granular formulations can be prepared by impregnating a solid such as granular fuller's earch, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5 to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salt and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate Phenols dinitro-o-(sec-butyl)phenol and its salts
pentachlorophenol and its salts Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether Anilides N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil Nitriles 2,6-dichlorobenzonitrile
diphenylacetonitrile
3,5-dibromo-4-hydroxybenzonitrile 3,5-diiodo-4-hydroxybenzonitrile Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazin-(4)3H-one-2,2-dioxide 6,7-dihydrodipyridol[1,2-a:2',-c]pyrazidinium salts
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The diphenyl ethers of the invention or their precursors can be prepared by reacting a suitably substituted phenol, or the potassium or sodium salt of the phenol, with a suitably substituted halobenzene, such as a chloro- or fluorobenzene, in the presence of an alkaline agent.

The following examples will further illustrate the invention but are not intended to limit it in any way. In Table I, typical phenyl ethers of the invention are listed, with their melting points and elemental analyses. Specific, illustrative preparations of the compounds of Examples 3, 7, 10, 19, 21, 25, 26, 37, 47, 48, 49, 51, 55, and 56 are described after Table I.

TABLE I

Diphenyl Ethers - Physical Data

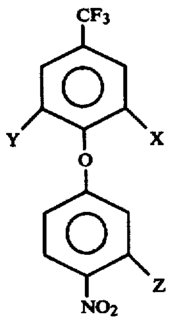

| Example No. | X | Y | Z | m.p. (°C.) | Analysis | | | | | |
|---|---|---|---|---|---|---|---|---|---|---|
| | | | | | | % C | % H | % N | % Cl | % F |
| 1 | H | H | $OC_2H_5$ | 72–75 | found | 54.67 | 3.75 | 4.19 | | 15.25 |
| | | | | | reqs. | 55.05 | 3.70 | 4.28 | | 17.42 |
| 2 | Cl | H | $OCH_3$ | 95–100 | found | 48.78 | 2.89 | 4.01 | 9.65 | 14.91 |
| | | | | | reqs. | 48.33 | 2.61 | 4.03 | 10.20 | 16.40 |
| 3 | Cl | H | $OC_2H_5$ | 83–84 | found | 49.85 | 3.33 | 3.68 | 9.90 | 15.51 |
| | | | | | reqs. | 49.80 | 3.07 | 3.87 | 9.80 | 15.75 |
| 4 | Cl | H | $OC_3H_7$—i | 49.5–51 | found | 51.02 | 3.58 | 3.52 | 9.62 | 15.58 |
| | | | | | reqs. | 51.18 | 3.49 | 3.73 | 9.42 | 15.16 |
| 5 | Cl | H | $OC_3H_7$—n | 75–76 | found | 51.36 | 3.60 | 3.62 | 9.34 | 15.00 |
| | | | | | reqs. | 51.18 | 3.49 | 3.73 | 9.42 | 15.16 |
| 6 | Cl | H | $OC_4H_9$—n | 51–52 | found | 52.07 | 4.03 | 3.38 | 9.28 | 14.65 |
| | | | | | reqs. | 52.42 | 3.88 | 3.59 | 9.10 | 14.63 |
| 7 | CN | H | $OC_2H_5$ | 143–145 | found | 54.84 | 3.36 | 8.01 | | 15.85 |
| | | | | | reqs. | 52.18 | 3.01 | 7.61 | | 15.48 |
| 8 | CN | H | $OCOC_3H_7$—n | 96.5–98 | found | 55.70 | 3.65 | 7.56 | | |
| | | | | | reqs. | 55.74 | 3.58 | 7.65 | | 15.56 |
| 9 | CN | H | $CH_3$ | 86–88.5 | found | 55.95 | 2.80 | 8.62 | | 17.68 |
| | | | | | reqs. | 55.90 | 2.81 | 8.72 | | 17.69 |
| 10 | Cl | H | OH | 68–70 | found | 47.07 | 2.11 | 4.00 | 10.76 | 17.00 |
| | | | | | reqs. | 46.79 | 2.12 | 4.20 | 10.63 | 17.08 |
| 11 | Cl | H | $OCH_2CF_3$ | 78–80 | found | 43.30 | 1.77 | 3.22 | 8.60 | 27.60 |
| | | | | | reqs. | 43.35 | 1.94 | 3.37 | 8.54 | 27.40 |
| 12 | Cl | H | $OCH_2CH{=}CH_2$ | 76.78.5 | found | 51.76 | 2.77 | 3.75 | 9.51 | 15.32 |
| | | | | | reqs. | 5.42 | 2.97 | 3.75 | 9.48 | 15.25 |
| 13 | Cl | H | $OCH_2C{\equiv}CH$ | 89–93 | found | 51.83 | 2.22 | 3.52 | 9.61 | 15.31 |
| | | | | | reqs. | 51.70 | 2.44 | 3.77 | 9.54 | 15.33 |
| 14 | Cl | H | $OCH_2CH_2C{\equiv}CCH_3$ | 93–94 | found | 53.99 | 2.95 | 3.35 | 8.93 | 14.12 |
| | | | | | reqs. | 54.10 | 3.28 | 3.50 | 8.87 | 14.25 |
| 15 | Cl | H | $OCH_2CH_2OH$ | 76–77 | found | 47.53 | 2.92 | 3.55 | 9.88 | 14.98 |
| | | | | | reqs. | 47.70 | 2.94 | 3.71 | 9.38 | 15.09 |
| 16 | Cl | H | $OCH_2CH_2OC_2H_5$ | 62–64 | found | 50.75 | 3.82 | 3.37 | 8.48 | 14.00 |
| | | | | | reqs. | 50.32 | 3.73 | 3.45 | 8.74 | 14.05 |
| 17 | Cl | H | $OCH_2CH_2N(CH_3)_2$ | oil | found | 50.30 | 3.76 | 6.42 | 9.19 | 13.80 |
| | | | | | reqs. | 50.44 | 3.98 | 6.92 | 8.76 | 14.08 |
| 18 | Cl | H | $OCOCH_3$ | 85–89 | found | 47.82 | 2.50 | 3.65 | 9.58 | 14.79 |

TABLE I-continued

Diphenyl Ethers - Physical Data

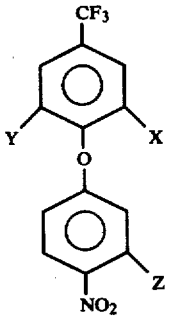

| Example No. | X | Y | Z | m.p. (°C.) | | Analysis % C | % H | % N | % Cl | % F |
|---|---|---|---|---|---|---|---|---|---|---|
| | | | | | reqs. | 47.90 | 2.42 | 3.73 | 9.44 | 15.20 |
| 19 | Cl | H | $NHC_2H_5$ | 82–83 | found | 50.01 | 3.23 | 7.82 | 9.95 | 15.48 |
| | | | | | reqs. | 49.94 | 3.35 | 7.77 | 9.83 | 15.80 |
| 20 | Cl | H | $N(CH_3)_2$ | 82–83 | found | 50.27 | 3.46 | 7.95 | 9.62 | 15.50 |
| | | | | | reqs. | 49.97 | 3.35 | 7.77 | 9.83 | 15.80 |
| 21 | Cl | H | $N(C_2H_5)_2$ | *170° C./0.01 mm | found | 52.80 | 3.89 | 7.10 | 9.25 | 14.58 |
| | | | | | reqs. | 52.50 | 4.15 | 7.20 | 9.12 | 14.68 |
| 22 | Cl | H | $NHCH_2CH_2OH$ | 85–87 | found | 46.22 | 3.33 | 7.06 | 8.50 | 15.30 |
| | | | | | reqs. | 47.82 | 3.21 | 7.44 | 9.42 | 15.13 |
| 23 | Cl | H | $OCH_2CO_2H$ | 94–96 | found | 45.96 | 2.21 | 3.71 | 9.17 | 13.99 |
| | | | | | reqs. | 46.00 | 2.32 | 3.57 | 9.05 | 14.56 |
| 24 | Cl | H | $OCH_2CO_2C_2H_5$ | 76–77 | found | 48.49 | 2.93 | 3.25 | 8.58 | 13.65 |
| | | | | | reqs. | 48.60 | 3.13 | 3.34 | 8.46 | 13.62 |
| 25 | Cl | H | $OCH(CH_3)CO_2H$ | 108–109 | found | 47.34 | 2.63 | 3.52 | 8.78 | 13.70 |
| | | | | | reqs. | 47.35 | 2.73 | 3.45 | 8.73 | 14.05 |
| 26 | Cl | H | $OCH(CH_3)CO_2C_2H_5$ | 71–72.5 | found | 49.78 | 3.40 | 3.07 | 8.31 | 12.90 |
| | | | | | reqs. | 49.85 | 3.49 | 3.23 | 8.18 | 13.15 |
| 27 | Cl | H | $NH_2$ | 85.5–89.5 | found | 48.6 | 2.87 | 8.01 | 10.37 | 17.09 |
| | | | | | reqs. | 46.93 | 2.42 | 8.42 | 10.66 | 17.14 |
| 28 | Cl | H | 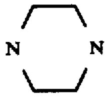 | *180–185/ 0.04 mm | found | 50.61 | 3.39 | 6.80 | 8.95 | 13.71 |
| | | | | | reqs. | 50.70 | 3.50 | 6.96 | 8.80 | 14.15 |
| 29 | Cl | H | $OCH_2CH_2C{\equiv}CH$ | 104–105.5 | found | 52.67 | 3.05 | 3.44 | 9.41 | 14.33 |
| | | | | | reqs. | 53.00 | 2.87 | 3.63 | 9.20 | 14.80 |
| 30 | Cl | H | $OCH(CH_3)C{\equiv}CH$ | 40–42 | found | 52.59 | 2.77 | 3.61 | 9.66 | 15.27 |
| | | | | | reqs. | 53.00 | 2.87 | 3.63 | 9.20 | 14.80 |
| 31 | Cl | H | $OCH_2CH_2COCH_3$ | 74–76 | found | 50.44 | 3.27 | 3.36 | 8.81 | 14.49 |
| | | | | | reqs. | 50.60 | 3.25 | 3.47 | 8.75 | 14.12 |
| 32 | Cl | H | $OCH(CH_3)COCH_3$ | oil | found | 48.07 | 3.26 | 3.17 | 8.18 | 14.26 |
| | | | | | reqs. | 50.60 | 3.25 | 3.47 | 8.75 | 14.12 |
| 33 | Cl | H | $OCONHCH_3$ | 85–88 | found | 45.57 | 3.21 | 8.02 | 9.48 | 14.76 |
| | | | | | reqs. | 46.10 | 2.58 | 7.18 | 9.08 | 14.60 |
| 34 | Cl | H | $NHCOC_2H_5$ | oil | found | 49.50 | 3.14 | 7.01 | 9.12 | 14.71 |
| | | | | | reqs. | 49.40 | 3.12 | 7.20 | 9.12 | 14.68 |
| 35 | Cl | H | $NHCOCH_2Cl$ | oil | found | 44.51 | 1.85 | 6.60 | 17.34 | 14.90 |
| | | | | | reqs. | 44.03 | 2.22 | 6.85 | 17.33 | 13.93 |
| 36 | Cl | H | $CH_3$ | *135° C./ 0.08 mm | found | 50.91 | 2.81 | 4.31 | 10.63 | 16.95 |
| | | | | | reqs. | 50.70 | 2.73 | 4.22 | 10.69 | 17.19 |
| 37 | Cl | H | Cl | *153° C./ 0.24 mm | found | 44.15 | 1.58 | 4.09 | 18.13 | 18.48 |
| | | | | | reqs. | 44.34 | 1.72 | 3.98 | 20.14 | 16.19 |
| 38 | Cl | H | 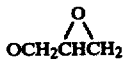 | 49–53 | found | 47.88 | 2.50 | 3.32 | 10.58 | 14.82 |
| | | | | | reqs. | 49.30 | 2.84 | 3.60 | 9.11 | 14.63 |
| 39 | Cl | H | $OCH_2CHOHCH_2OH$ | 59–64 | found | 47.49 | 3.32 | 3.35 | 8.88 | 14.73 |
| | | | | | reqs. | 49.00 | 3.35 | 3.58 | 9.05 | 14.58 |
| 40 | Cl | H | $OCH_2CH_2SCH_3$ | 42–45 | found | 47.09 | 2.95 | 3.34 | 8.80 | 14.05 |
| | | | | | reqs. | 47.12 | 3.21 | 3.44 | 8.69 | 13.98 |
| 41 | Cl | H | $N(C_3H_7\text{—}n)_2$ | oil | found | 54.04 | 4.62 | 6.34 | 8.71 | 13.55 |
| | | | | | reqs. | 54.75 | 4.84 | 6.72 | 8.50 | 13.67 |
| 42 | Cl | H | $OCH_2CH_2SO_2CH_3$ | 127.5–129.5 | found | 43.53 | 2.71 | 2.99 | 8.27 | 13.19 |
| | | | | | reqs. | 43.69 | 2.98 | 3.19 | 8.06 | 12.96 |
| 43 | Cl | H | $N(CH_3)CH_2CH_2OH$ | oil | found | 48.95 | 3.65 | 7.18 | 9.29 | 14.87 |
| | | | | | reqs. | 49.18 | 3.61 | 7.17 | 9.07 | 14.59 |
| 44 | Cl | H | $NHCONHCH_3$ | 204–208 | found | 46.52 | 2.56 | 10.76 | 9.40 | 14.47 |
| | | | | | reqs. | 46.22 | 2.85 | 10.78 | 9.10 | 14.63 |

TABLE I-continued

Diphenyl Ethers - Physical Data

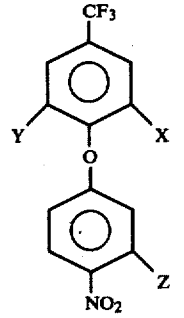

| Example No. | X | Y | Z | m.p. (°C.) | | Analysis % C | % H | % N | % Cl | % F |
|---|---|---|---|---|---|---|---|---|---|---|
| 45 | Cl | H | $NHCOSC_2H_5$ | 111-112 | found | 45.76 | 2.88 | 6.77 | 8.58 | 13.24 |
| | | | | | reqs. | 45.66 | 2.88 | 6.66 | 8.42 | 13.55 |
| 46 | Cl | H | $N(COSC_2H_5)_2$ | 99-100 | found | 45.08 | 3.14 | 5.35 | 7.20 | 11.03 |
| | | | | | reqs. | 44.84 | 3.17 | 5.50 | 6.97 | 11.20 |
| 47 | Cl | H | CN* | 95-103 | found | 49.92 | 1.82 | 7.68 | 11.57 | 15.69 |
| | | | | | reqs. | 49.05 | 1.77 | 8.18 | 10.35 | 16.65 |
| 48 | Cl | H | $CO_2H$ | 140-150 | found | 46.26 | 1.86 | 3.45 | 11.03 | 14.48 |
| | | | | | reqs. | 46.50 | 1.95 | 3.87 | 9.82 | 15.78 |
| 49 | Cl | H | $CO_2CH_3$ | oil | found | 47.77 | 2.64 | 3.48 | 10.49 | 12.93 |
| | | | | | reqs. | 47.90 | 2.42 | 3.73 | 9.45 | 15.20 |
| 50 | Cl | H | $OCH(CH_3)CO_2CH_3$ | 68-70 | found | 48.58 | 2.98 | 3.15 | 8.58 | 13.73 |
| | | | | | reqs. | 48.60 | 2.98 | 3.35 | 8.43 | 13.58 |
| 51 | Cl | H | $OCH(CH_3)CONH_2$ | 108-111 | found | 47.61 | 3.21 | 6.70 | 8.98 | 14.37 |
| | | | | | reqs. | 47.50 | 2.99 | 6.93 | 8.78 | 14.10 |
| 52 | Cl | H | $OCH(CH_3)CONHCH_3$ | 121-126 | found | 48.68 | 3.53 | 6.54 | 8.78 | 13.72 |
| | | | | | reqs. | 48.80 | 3.37 | 6.70 | 8.48 | 13.62 |
| 53 | Cl | H | $OCH(CH_3)CON(CH_3)_2$ | 83-85 | found | 50.17 | 3.78 | 6.25 | 8.37 | 13.22 |
| | | | | | reqs. | 50.00 | 3.73 | 6.48 | 8.20 | 13.18 |
| 54 | Cl | H | $N(C_2H_5)CH_2CH_2OH$ | | found | 50.44 | 3.99 | 6.92 | 8.76 | 14.08 |
| | | | | | reqs. | 50.27 | 4.10 | 6.89 | 8.86 | 14.18 |
| 55 | Cl | H | $N(C_2H_5)CONHCH_3$ | 127.5-128.5 | found | 49.51 | 3.91 | 9.95 | 8.64 | 12.60 |
| | | | | | reqs. | 48.87 | 3.62 | 10.06 | 8.49 | 13.64 |
| 56 | Cl | Cl | $OC_2H_5$ | 100.5-102 | found | 45.26 | 2.43 | 3.36 | 18.00 | 12.33 |
| | | | | | reqs. | 45.47 | 2.54 | 3.54 | 17.90 | 14.39 |

*boiling point

EXAMPLE 3

Preparation of 2-Chloro-α,α,α-trifluoro-p-tolyl-3-ethoxy-4-nitrophenyl ether Method A a. 1,3-Bis(2-chloro-α,α,α-trifluoro-p-tolyloxy)benzene A solution of potassium hydroxide (3.26 g. 0.05 mole, 85%) in water (~3 g.) is added slowly dropwise to a solution of resorcinol (2.75 g. 0.025 mole) and 3,4-dichloro-α,α,α-trifluorotoluene (10.75 g. 0.05 mole) in sulfolane (125 ml) at 150°-160° C., with stirring. When the addition is complete, the strongly colored reaction mixture is stirred at 150°-160° C. overnight, then cooled, diluted with benzene (200 ml), and washed cautiously with water (700 ml). Hexane (200 ml) is added and the mixture washed with water (600 ml), dilute sulfuric acid (600 ml), dilute sodium hydroxide solution (600 ml), and water (600 ml), dried, and the solvent removed to give 1,3-bis(2-chloro-α,α,α-trifluoro-p-tolyloxy)benzene (8.6 g 65%) b.p. 160°-70° C./0.1 mm.

b. 1,3-Bis(2-chloro-α,α,α-trifluoro-p-tolyloxy)-4-nitrobenzene 1,3-Bis(2-chloro-α,α,α-trifluoro-p-tolyloxy)benzene (12 g. 0.0255 mole) is added to a mixture of concentrated nitric acid (12 g.) and sulfuric acid (15 g.) at 5° C. The temperature is then allowed to rise to 25°-30° C. with manual stirring and mild ice bath cooling and after 10-20 minutes, the oil solidifies. The mixture is taken up in water/benzene (400 ml)/hexane (400 ml) and the organic phase is washed with water, dried, filtered through activated silica gel (~20 g.), and the solvents removed. The residue is recrystallized from isopropanol to give 1,3-bis(2-chloro-α,αα-trifluoro-p-tolyloxy)-4-nitrobenzene, (7.4 g. 56%) m.p. 110°-111.5° C.

c. 2-Chloro-α,α,α-trifluoro-p-tolyl-3-ethoxy-4-nitrophenyl ether

A 10% solution of potassium hydroxide in ethanol (10 ml) is added to a solution of 1,3-bis(2-chloro-α,α,α-trifluoro-p-tolyloxy)-4-nitrobenzene (2 g. 0.0039 mole) in dioxane (20 ml). After 40 minutes at room temperature, the solution is heated to 45° C. for 8 minutes, then cooled, diluted with benzene (50 ml) and hexane (50 ml) and washed with water (3×100 ml), dried, and the solvents removed. The residue is recrystallized from ispropanol to give 2-chloro-α,α,α-trifluoro-p-tolyl-3-ethoxy-4-nitrophenylether (1.21 g. 86%) m.p. 83°-84° C.

Method B a. 2-Chloro-α,α,α-trifluoro-p-tolyl-3-hydroxyphenyl ether

A mixture of the di-potassium salt of resorcinol (186.3 g., 1 mol), 3,4-dichloro-α,α,α-trifluorotoluene (53.7 g., 0.25 L mol), and sulfolane (100 ml.) is stirred for 30 hours at 140°-160° C.

Benzene (500 ml) and water (200 ml) are added and the organic phase is washed with water (3×200 ml), diluted with hexane (500 ml) and washed again with water, dried, filtered through activated silica gel (15 g.), the solvents removed, and the residue distilled to give 2-chloro-α,α,α-trifluoro-p-tolyl-3-hydroxyphenyl ether (45.1 g., 62%) b.p. 112°-124° C./0.3 mm.

b. 2-Chloro-α,α,α-trifluoro-p-tolyl-3-acetoxyphenyl ether

A mixture of 2-α,α,α-trifluoro-p-tolyl-3-hydroxyphenylether (184 g.) and acetic anhydride (334 g.) is heated on a steam bath for 1 hour and cooled. The mixture is washed with 5% sodium carbonate solution (2×500 ml.) and distilled to give 2-chloro-α,α,α-trifluoro-p-tolyl-3-acetoxyphenyl ether (84 g., 40%) b.p. 107°-117° C./0.09 mm.

c. 2-Chloro-α,α,α-trifluoro-p-tolyl-3-acetoxy-4-nitrophenyl ether

A solution of 2-chloro-α,α,α-trifluoro-p-tolyl-3-acetoxyphenyl ether (249 g., 0.75 mol) in 1,2-dichloroethane (1200 ml.) is stirred 2.2 hours at 20°-30° C. with a cooled mixture of concentrated sulfuric acid (276 g.) and nitric acid, 70% (227 g.). Hexane (700 ml.) is added and the oil layer washed once with water, 3 times with dilute sodium bicarbonate, and once more with water, dried, filtered through activated silica gel (~40 g.), the solvents removed. The product is crystallized from hexane-benzene to give 2-chloro-α,α,α-trifluoro-p-tolyl-3-acetoxy-4-nitrophenyl ether (207.5 g., 73%) m.p. 83°-89° C.

d. 2-Chloro-α,α,α-trifluoro-p-tolyl-3-hydroxy-4-nitrophenyl ether

A solution of 2-chloro-α,α,α-trifluoro-p-tolyl-3-acetoxy-4-nitrophenyl ether (204.9 g., 0.545 mol) in methanol (2900 ml.) is stirred 1 hour at 20° C. with potassium carbonate (103 g., 0.745 mol). Ninety percent of the methanol is removed; and benzene (1 liter), 7-8% sulfuric acid solution (1600 ml.) are added and stirred 1.5 hours at 25° C. The oil layer is washed twice more with water (200 ml. each), dried, filtered through activated silica gel (40 g.,), the solvents removed, and the residue crystallized in hexane to give 2-chloro-α,α,α-trifluoro-p-tolyl-3-hydroxy-4-nitrophenyl ether (165.3 g. 90%) m.p. 68.5°-73° C.

e. 2-Chloro-α,α,α-trifluoro-p-tolyl-3-ethoxy-4-nitrophenyl

A solution of 2-chloro-α,α,α-trifluoro-p-trifluoro-p-tolyl-3-hydroxy-4-nitrophenyl ether (60 g., 0.018 mol, 73% pure) and dimethylformamide (100 g.) is converted to the potassium phenoxide and stirred with ethyl bromide (35 g., 0.32 mol) 3 hours at 60° C. and 5 hours at 80° C. Perchlorethylene (150 g.) is added and the solution washed twice with water (~250 ml. each) at 50° C. The solvents are removed to give 2-chloro-α,α,α-trifluoro-p-tolyl-3-ethoxy-4-nitrophenyl ether (56 g., 83%, 71% pure).

EXAMPLE 7

Preparation aof 2-Cyano-60,α,α-trifluoro-p-tolyl-3-ethoxy-4-nitrophenyl ether A solution of potassium hydroxide (2.6 g., 0.04 mole) 87.3% pure and 3ethoxy-4-nitrophenol (7.3 g., 0.04 mole) in methanol (30 ml) is stripped to dryness under reduce pressure. A residue of potassium 3-ethoxy-4-nitrophenoxide is dissolved in sulfolane (200 g.) and 4-chloro-3-cyano-benzotrifluoride (8.2 g., 0.04 mole) is added. Gas-liquid chromotography shows the reaction to be complete after stirring at 110° C. for 4½ hours and 135° C. for 2½ hours. The reaction mixture is cooled and poured into deionized water and the precipitate which forms is filtered off and air dried. Recrystallization from isopropanol yields 2-cyano-α,α,α-trifluoro-p-tolyl-3-ethoxy-4-nitrophenyl ether (7.4 g. 53%) m.p. 143°-145° C.

EXAMPLE 19

Preparation of 2-Chloro-α,α,α-trifluoro-p-tolyl-3-ethylamino4nitrophenyl ether A solution of 1,3-bis(2chloro-α,α,α-trifluoro-p-tolyloxy)-4-nitrobenzene(12.8 g. 0.025 mol), and ethylamine (6.7 g. 0.15 mol) in dioxane (120 ml.) is heated in a pressure bottle 4.5 hours at 50°-55° C. and 4.3 hours at 90°-95° C. Benzene (200 ml.), hexane (70 ml.) and water (500 ml.) are added and the organic phase is washed with water (500 ml.), 10% sodium bicarbonate solution (200 ml.) and water (200 ml), dried, filtered through activated silica gel (25 g.), the solvents removed, and the residue is crystallized from hexane to give 2-chloro-α,α,α-trifluoro-p-tolyl-3-ethylamino-4-nitrophenyl ether (7.9 g. 88%) m.p. 82°-83° C.

EXAMPLE 21

Preparation of 2-Chloro-α,α,α-trifluoro-p-tolyl-3-diethylamino-4-nitrophenyl ether A solution of 1,3-bis(2-chloro-α,α,α-trifluoro-p-tolyloxy)-4-nitrobenzene (12.8 g. 0.025 mol) in p-dioxane (130 ml.) is heated under reflux for 26 hours at 65°-95° C. with diethylamine (50 g. 0.66 mol). Benzene (~200 ml.) and water (~500 ml.) are added followed by hexane (~70 ml.) and the layer is separated, washed with water (500 ml), 10% sodium bicarbonate solution (200 ml), and water (200 ml.), dried, filtered through activated silica gel (~25 g.), the solvents removed. The residual oil is distilled in vacuo to give 2-chloro-α,α,α-trifluoro-p-tolyl-3-diethylamino-4-nitrophenyl ether (8.15 g 84%) b.p. 180°-190° C./0.01 mm.

EXAMPLE 25

Preparation of 2-Chloro-α,α,α-trifluoro-p-tolyl-3-(1-carboxyethoxy)-4-nitrophenyl ether 2-Chloro-α,α,α-trifluoro-p-tolyl-3-(1-carbethoxyethoxy)-4-nitrophenyl ether (8.6 g. 0.02 mol), potassium hydroxide 86% (2.6 g. 0.04 mol), ethanol (8 ml.), dioxane (8 ml.), and water (100 ml.) are heated at 90°-95° C. for 30 minutes. Ether (200 ml.) and water (200 ml.) are added and the mixture acidified with dilute sulfuric acid, the water layer extracted three times with ether (200 ml. each), dried and the ether removed to give 2-chloro-60,α,α-trifluoro-p-tolyl-3-(1-carboxyethoxy)-4-nitrophenyl ether (6.4 g. 79%) m.p. 108°-109° C.

EXAMPLE 26

Preparation of 2-Chloro-α,α,α-trifluoro-p-tolyl-3-(1-carbethoxyethoxy)-4-nitrophenyl ether Potassium 2-nitro-5-(2-chloro-α,α,α-trifluoro-p-tolyloxy)phenoxide (7.4 g. 0.02 mol), ethyl 2-bromopropionate (3.6 g. 0.02 mol) and the sulfolane (50 ml.) are heated 1.5 hours at 90°-95° C. Benzene (100 ml.) and hexane (100 ml.) are added and the solution is washed with dilute sodium carbonate solution then with water, dried, and the solvents removed. The residue is crystallized from pentane to give 2-chloro-α,α,α-trifluoro-p-tolyl-3-(1-carbethoxyethoxy)-4-nitrophenyl ether (6.2 g., 71%) m.p. 71°-74° C.

EXAMPLE 27

Preparation of
2-chloro-α,α,α-trifluoro-p-tolyl-3-chloro-4-nitrophenyl ether a. 3-Chloro-4-nitrofluorobenzene m-Chlorofluorobenzene (240 g. 1.85 moles) is added to a mixture of sulfuric acid (185 g. 1.85 moles) and nitric acid (166 g., 1.85 moles) at −5° C. in 3.5 hours, stirred 13 hours, then benzene (200 ml.) and hexane (200 ml.) are added. The extract is washed with water (1×300 ml.), sodium carbonate solution (1×300 ml.), and water (1×300 ml.), dried and the solvents removed. The residue is distilled to give 138 g. of mixed isomers. The 4-nitro isomer crystallizes and is filtered off to give 3-chloro-4-nitrofluorobenzene (51 g. 16.7%) m.p. 36°-38° C.

EXAMPLES 47-49

Preparation of
2-Chloro-α,α,α-trifluoro-p-tolyl-3-carbomethoxy-4-nitrophenyl ether a. 3-Cyano-4-nitrofluorobenzene m-Fluorobenzonitrile 96.8 g., 0.8 mole) is added in two and one-half hours to a mixture of concentrated sulfuric acid (600 ml.) and potassium nitrate (80.9 g., 0.8 mole) at 3°-6° C., then allowed to warm to 25° C. The mixture is poured over cracked ice (3000 ml.), extracted with chloroform (5×250 ml.), dried and the solvent removed. The residue is extracted with pentane and dried to give 3-cyano-4-nitrofluorobenzene (115 g., 86.5%) m.p. 102°-104° C.

b. 2-Chloro-α,α,α-trifluoro-p-tolyl-3-cyano-4-nitrophenyl ether

The potassium phenoxide of 2-chloro-α,α,α-trifluoro-p-cresol (13.5 g 0.0688 mole) prepared in sulfolane at 5° C. is added to a solution of 3-cyano-4-nitrofluorobenzene (11.4 g., 0.0688 mole) in sulfolane at 120° C. in four hours, stirred 18 hours and cooled. Benzene (200 ml.) and hexane (100 ml) are added and the solution is water washed (5×250 ml.), dried, filtered and the solvents removed. The residue is crystallized to give 2-chloro-α,α,α-p-tolyl-3-cyano-4-nitrophenyl ether (16.3 g., 69%) m.p. 95°-103° C. 85% pure.

c. 2-Chloro-α,α,α-trifluoro-p-tolyl-3-carboxy-4-nitrophenyl ether

2-Chloro-α,α,α-trifluoro-p-tolyl-3-cyano-4-nitrophenyl ester (11.2 g. 0.0327 mole), acetic acid (25 ml.), and hydrobromic acid (12 mol. of 47.8% purity) are heated at 120° C., in a pressure bottle, for two days, poured over cracked ice and extracted with benzene (2×150 ml.). The benzene solution is dried, filtered, the solvent removed, and the residue crystallized from pentane to give 2-chloro-α,α,α-trifluoro-p-tolyl-3-carboxy-4-nitrophenyl ether (7.5 g. 63.5%) m.p. 140°-150° C., 85% pure.

d. 2-Chloro-α,α,α-trifluoro-p-tolyl-3-carbomethoxy-4-nitrophenylether

Hydrogen chloride is bubbled thru a solution of 2-chloro-α,α,α-trifluoro-p-tolyl-3-carboxy-4-nitrophenyl ether (2.3 g. 0.0064 mole) in methanol (50 ml.) for 10 hours at 32° C., stirred overnite and the solvent removed to give 2-chloro-α,α,α-trifluoro-p-tolyl-3-carbomethoxy-4-nitrophenyl ether (1.5 g. 40%)

EXAMPLE 51

Preparation of
2-Chloro-α,α,α-trifluoro-p-tolyl-3-(1-carbamoylethoxy)-4-nitrophenyl ether a. 2-Chloro-α,α,α-trifluoro-p-tolyl-3-(1-chloroformylethoxy)-4-nitrophenyl ether 2-Chloro-α,α,α-trifluoro-p-tolyl-3-(1-carboxyethoxy)-4-nitrophenyl ether (34.8 g. 0.086 mol), thionyl chloride (20.4 g. 0.172 mol), and benzene (150 ml.) are stirred 5 hours at 95° C. and 16 hours at 25° C. The benzene is removed to give 2-chloro-α,α,α-trifluoro-p-tolyl-3-(1-chloroformylethoxy)-4-nitrophenyl ether (33.4 g. 92%).

b. 2-Chloro-α,α,α-trifluoro-p-tolyl-3-(1-carbamoylethoxy)-4-nitrophenyl ether

A solution of 2-chloro-α,α,α-trifluoro-p-tolyl-3-(1-chloroformylethoxy)-4-nitrophenyl ether (4.2 g. 0.01 mol) in ether (50 ml.) is added to an ether solution (200 ml.) saturated with gaseous ammonia at zero temperatures. After 30 minutes, water (100 ml.) is added and the ether layer separated. The aqueous phase is extracted with ether (3×200 ml.) and the combined extracts dried, filtered through activated silica gel (~20 g.), and the solvent removed to give 2-chloro-α,α,α-trifluoro-p-tolyl-3-(1-carbamoylethoxy)-4-nitrophenyl ether (2.4 g. 60%) m.p. 108°-111° C.

EXAMPLE 55

Preparation of
2-Chloro-α,α,α-trifluoro-p-tolyl-3-(3-methyl-1-ethylureido)-4-nitrophenyl ether a. 2-Chloro-α,α,α-trifluoro-p-tolyl-3-(N-ethylchloroformamido)-4-nitrophenyl ether A mixture of 2-chloro-α,α,α-trifluor-p-tolyl-3-ethylamino-4-nitro phenyl ether (3.6 g. 0.01 mol), phosgene (18.9 g. 0.19 mol), 2,6-lutidine (2.2 g. 0.02 mol), and benzene (~130 ml.) are heated in a pressure bottle 64 hours at 90°-95° C. The mixture is cooled, filtered and the solvent removed to give 2-chloro-α,α,α-trifluoro-p-tolyl-3-(N-ethylchloroformamido)-4-nitrophenyl ether.

b. 2-Chloro-α,α,α-trifluoro-p-tolyl-3-(3-methyl-1-ethylureido)-4-nitrophenyl ether A solution of 2-chloro-α,α,α-trifluoro-p-tolyl-3-(N-ethylchloroformamide)-4-nitrophenyl ether (4.4 g., 0.01 mol), methylamine (3.3 g. 0.11 mol) and benzene (~60 ml.) is allowed to stand 25 minutes at zero °C., filtered, and the solvent removed. Benzene (~100 ml.) and hexane (50 ml.) are added and the solution is washed with water (100 ml.) and aqueous 10% sodium carbonate solution (2×100 ml.), dried, and the product abosrbed on activated silica gel (~25 g.). The product is eluted with a mixture of benzene (400 ml.) and methanol (40 ml) the solvents removed and the product recrystallized to give 2-chloro-α,α,α-trifluoro-p-tolyl-3-(3-methyl-1-ethylureido)-4-nitrophenyl ether (2.6 g. 62%) m.p. 127.5°-128.5° C.

EXAMPLE 56

Preparation of 2,6-Dichloro-α,α,α-trifluoro-p-tolyl-3-ethoxy-4-nitrophenyl ether a. 3,4-Dichloro-5-nitro-α,α,α-trifluorotoluene 3,4-Dichloro-α,αα-trifluorotoluene (862 g. 4.0 mols) is added to a stirred mixture of concentrated sulfuric acid (4400 g.) and nitric acid (3400 g.) at 35° C. The mixture is stirred 70 minutes at 95° C., and allowed to separate. The oil layer is washed once with waer and twice with 5% sodium carbonate solution, dried, and fractionally distilled to give 3,4-dichloro-5-nitro-α,αα-trifluorotoluene (188 g. 18%) b.p. 115°-118° C./15 mm, 88% pure.

b. 5-Amino-3,4-dichloro-α,α,α-trifluorotoluene 500 ml. of an ethanolic solution containing 3,4-dichloro-5-nitro-α,α,α-trifluorotoluene (188 g. 0.72 mol), and platinum oxide (Adam's catalyst) (0.2 g.) is reduced at room temperature in a low pressure hydrogenation apparatus to give 5-Amino-3,4-dichloro-α,α,α-trifluorotoluene (129.9 g. 78%) b.p. 65°-70° C./1-2 mm.

c. 3,4,5-Trichloro-α,α,α-trifluorotoluene

A solution of sodium nitrite (39 g.) in water (85 ml.) is added over 1 hour to a solution of 5-amino-3,4-dichloro-α,α,α-trifluorotoluene (117.5 g., 0.51 mol) in 1700 ml. concentrated hydrochloric acid at −6° C. and the solution stirred for 1 hour then filtered. The filtrate is added to a solution of cuprous chloride (76.5 g.) in concentrated hydrochloric acid (500 ml.) over 5 minutes at 0° to 8° C. and gradually heated to 80° C. over 80 minutes. The reaction mixture is cooled to 35° C. and extracted with hexane (2×300 ml.). The extract is washed with water, 2% sodium hydroxide solution, dried and distilled to give 3,4,5-trichloro-α,α,α-trifluorotoluene (70 g., 55%) b.p. 82°-86° C./10 mm, 95% pure.

d. 1,3-Bis(2,6-dichloro-α,α,α-trifluoro-p-tolyloxy)benzene

A mixture of 3,4,5-trichloro-60,α,α-trifluorotoluene (10 g. 0.04 mol), and the dipotassium salt of 1,3-dihydroxybenzene (4 g. 0.021 mol) in 150 ml. sulfolane is stirred and heated 70 minutes at ~120° C. The cooled reaction mixture is diluted with benzene (350 ml.) and washed once with water (1 l). Hexane (200 ml.) is added, and the solution washed with water (3×500 ml.) dried, filtered through activated silica gel (~25 g.), and the solvents removed. The residual oil is crystallized from a mixture of pentane and benzene to give 1,3-bis(2,6-dichloro-α,α,α-trifluoro-p-tolyoxy)benzene (5.3 g. 49%) m.p. 121°-122° C.

e. 1,3-Bis(2,6-dichloro-α,α,α-trifluoro-p-tolyloxy)-4-nitrobenzene

A cooled mixture of concentrated sulfuric acid (6.5 ml.) and nitric acid (4.4 ml.) is added with stirring to an ice cold solution of 1,3-bis(2,6-dichloro-60,α,α-trifluoro-p-tolyoxy)-benzene (11.1 g. 0.021 mol) in 1,2-dichlorethane (30 ml.). After 30 minutes at room temperature, the phases are allowed to separate and the organic phase washed twice with water. Benzene (200 ml.) is added and the solution washed twice with dilute sodium carbonate solution, dried, filtered through activated silica gel (~25 g.), and the solvents removed. The residual crystals are triturated with pentane, filtered, and dried to obtain 1,3-bis(2,6-dichloro-α,α,α-trifluoro-p-tolyloxy)-4-nitrobenzene (9.9 g., 82%) m.p. 137.5°-140.5° C., 90% pure.

f. 2,6-Dichloro-α,α,α-trifluoro-p-tolyl-3-ethoxy-4-nitrophenyl ether

A solution of potassium hydroxide, 86% (1.9 g., 0.029 mol) in ethanol (20 ml.) is added to a solution of 1,3-bis(2,6-dichloro-α,α,α-trifluoro-p-toloxy)-4-nitrobenzene (8.0 g., 0.014 mol) in p-dioxane (70 ml.) and warmed 1 hour at 50° C. The solution is cooled and benzene (~250 ml.) is added and crystals of potassium 2-nitro-5-(2,6-dichloro-α,α,α-trifluoro-p-tolyloxy)-phenoxide (2.9 g. 52%) are collected. Treatment with acid yields the free phenol, 2,6-dichloro-α,α,α-trifluoro-p-tolyl-3-hydroxy-4-nitrophenyl ether (2.0 g. 40%) m.p. 84.5°-86.5° C. The phenol (1.7 g. 0.0046 mol) is reconverted to the potassium salt, dissolved in dimethylformamide (20 ml.) and treated with ethyl iodide (1.2 g. 0.0077 mol) 2.5 hours at 50°-70° C. The reaction mixture is diluted with benzene (~100 ml.) and hexane (18 50 ml.), washed with water (3×100 ml.), dried, filtered through activated silica gel (~15 g.), and the solvents removed to give 2,6-dichloro-α,α,α-trifluoro-p-tolyl-3-ethoxy-4-nitrophenyl ether (0.8 g. 44%) m.p. 100.5°-102° C.

From the filtrate of the 2.9 g. of phenoxide there is recovered ethyl 2,6-dichloro-α,α,α-trifluoro-p-tolyl ether (3.0 g. 82%) b.p. 78° C./5 mm, and an additional amount of the product 2,6-dichloro-α,α,α-trifluoro-p-tolyl-3-ethoxy-4-nitrophenyl ether (0.35 g. 6%) m.p. 88°-93° C.

EXAMPLES 57 TO 72

Following the procedures of Examples 1 to 56, other diphenyl ethers of Formula I are prepared. Among the compounds which are prepared by these procedures are:

α,αα,α',α',α'-hexafluoro-2,4-xylyl-3-ethoxy-4-nitrophenyl ether $α^4$,$α^4$,$α^4$-trifluoro-2,4-xylyl-3-n-propoxy-4-nitrophenyl ether, 2-chloro-6,α,α,α-tetrafluoro-p-tolyl-3-ethyl-4-nitrophenyl ether, 2-iodo-α,α,α-trifluoro-p-tolyl-3-methoxy-4-nitrophenyl ether, 2-chloro-6-cyano-α,α,α-trifluoro-p-tolyl-3-methylthio-4-nitrophenyl ether, 2-bromo-$α^4$,$α^4$,$α^4$-trifluoro-4,6-xylyl-3-ethoxy-4-nitrophenyl ether, 2-chloro-α,α,α,α',α',α'-hexafluoro-4,6-xylyl-3-methoxy-4-nitrophenyl ether, 2-bromo-α,α,α-trifluoro-p-tolyl-3-ethoxy-4-nitrophenyl ether, 2-chloro-α,α,α-trifluoro-p-tolyl-3-n-butyl-4-nitrophenyl ether, 2-chloro-α,α,α-trifluoro-p-tolyl-31-bromo-4-nitrophenyl ether, 2-cyano-α,α,α-trifluoro-p-tolyl-3-acetoxy-4-nitrophenyl ether, 2-bromo-α,α,α-trifluoro-p-tolyl-3-diethylamino-4-nitrophenyl ether, 2,6-dichloro-α,αα-trifluoro-p-tolyl-3-ethylamino-4-nitrophenyl ether, 2-cyano-α,α,α-trifluoro-p-tolyl-3-(1-carbethoxyethoxy)-4-nitrophenyl ether, 2-cyano-α,αα-trifluoro-p-tolyl-3-carbomethoxy-4-nitrophenyl ether, and 2-bromo-α,α,α-trifluoro-p-tolyl-3-carboxy-4-nitrophenyl ether.

These diphenyl ethers have herbicidal properties.

It should be noted that the diphenyl ethers of the invention can also be named correctly using different systems of nomenclature. For example, the diphenyl ether of Example 3 can also be named as 2-cyano-4-trifluoromethyl-3'-ethoxy-4'-nitrodiphenyl ether. However, within the specification and claims of this invention the system of nomenclature exemplified in Examples 1-56 has been followed.

The following examples show the herbicidal properties of the diphenyl ethers of the invention.

EXAMPLE 73

This example shows the herbicidal activity of diphenyl ethers of the invention towards a number of common weeds. Using the procedure described below, diphenyl ethers were evaluated for control of the following weeds:

At 10 pounds per acre:

Monocots barnyardgrass (*Echinochloa crusgalli*)
crabgrass (Digitaria spp.)
nutsedge (*Cyperus esculentus*)
wild oats (*Avena fatua*)

Dicots bindween (*Convolvulus arvensis*)
curly dock (*Rumex crispus*)
velvetleaf (*Abutilon theophrasti*)
wild mustard (*Brassica haber*)

At 2 and 4 pounds per acre:

Monocots barnyardgrass (*Echinochloa crusgalli*)
**Bermudagrass (*Cynodon dactylon*)
crabgrass (Digitaria spp.)
*downy brome (*Bromus tectorum*)
foxtail (*Setaria faberii*)
Johnsongrass (*Sorghum halepense*)
nutsedge (*Cyperus esculentus*)
quackgrass (*Agropyron repens*)
*ryegrass (*Lolium perenne*)
*wild oats (*Avena fatus*)
*yellow millet (*Panicum miliceum*)

Dicots binweed (*Convolvulus arvensis*)
cocklebur (*Xanthium pensylvanicum*)
**coffeeweed (*Sesbania macrocarpa*)
*curly dock (*Rumex crispus*)
*lambsquarters (*Chenopodium album*)
morningglory (*Ipomoea purpurea*)
*pigweed (*Amaranthus retroflexus*)
**ragweed (*Ambrosia artemisiifolia*)
*smartweed (*Polygonum pensylvanicum*)
**tomato (*Lycopersicon esculentum*)
velvetleaf (*Abutilon theophrasti*)
*wild carrot (*Daucus carota*)
*wild mustard (*Brassica haber*)

*Examples 1 to 9 only
**Examples 10 to 56 only

The following test procedures is employed. Seeds of selected crops and weeds are planted in soil in flats. For preemergence tests, the flats are treated with the test compound immediately after the planting. For postemergence tests, the seeds are allowed to germinate, and after 2 weeks the flats are treated with the test compound. The compound to be evaluated is dissolved in acetone, diluted with water, and sprayed over the flats using a carrier volume equivalent to 50 gallons per acre at the rate of application (pounds per acre, lb/A.) specified in the tables. About 2 weeks after the application of the test compound, the state of growth of the plants is observed and the phytotoxic effect of the compound is evaluated. Table II gives the average percent control achieved by the test compounds in terms of the percent of the plants which are killed by the compounds.

TABLE II

| Compound of | | HERBICIDAL ACTIVITY (% control) | | | | | |
|---|---|---|---|---|---|---|---|
| | | Preemergence | | | Postemergence | | |
| Example No. | lb./A. | 10 | 4 | 2 | 10 | 4 | 2 |
| 1 | M* | 42 | 76 | | 82 | 57 | |
| | D* | 35 | 45 | | 100 | 58 | |
| 2 | M | 97 | 97 | | 100 | 99 | |
| | D | 100 | 80 | | 100 | 100 | |
| 3 | M | 99 | 89 | **84 | 100 | 99 | +96 |
| | D | 100 | 99 | **66 | 100 | 100 | +97 |
| 4 | M | | 98 | | | 80 | |
| | D | | 100 | | | 100 | |
| 5 | M | 97 | 84 | | 100 | 99 | |
| | D | 100 | 78 | | 100 | 100 | |
| 6 | M | 65 | 77 | | 97 | 91 | |
| | D | 70 | 55 | | 100 | 94 | |
| 7 | M | 61 | 65 | 65 | 100 | 75 | 82 |
| | D | 60 | 57 | 54 | 100 | 77 | 80 |
| 8 | M | 81 | 61 | 52 | 85 | 48 | 35 |
| | D | 82 | 57 | 46 | 100 | 80 | 66 |
| 9 | M | 99 | 90 | 81 | 100 | 97 | 82 |
| | D | 92 | 66 | 67 | 100 | 81 | 75 |
| 10 | M | | 70 | 66 | | 67 | 17 |
| | D | | 100 | 70 | | 98 | 85 |
| 11 | M | | 81 | 88 | | 82 | 100 |
| | D | | 98 | 99 | | 99 | 100 |
| 12 | M | | 86 | 72 | | 77 | 99 |
| | D | | 96 | 93 | | 100 | 100 |
| 13 | M | | 76 | 78 | | 77 | 100 |
| | D | | 90 | 72 | | 98 | 100 |
| 14 | M | | 64 | 30 | | 61 | 91 |
| | D | | 78 | 22 | | 94 | 100 |
| 15 | M | | 99 | 68 | | 79 | 76 |
| | D | | 100 | 90 | | 99 | 94 |
| 16 | M | | 86 | 67 | | 77 | 82 |
| | D | | 94 | 75 | | 96 | 94 |
| 17 | M | | 51 | 20 | | 45 | 39 |
| | D | | 84 | 31 | | 89 | 98 |
| 18 | M | | 67 | 99 | | 28 | 28 |
| | D | | 100 | 100 | | 86 | 98 |
| 19 | M | | 91 | 77 | | 84 | 94 |
| | D | | 96 | 91 | | 98 | 97 |
| 20 | M | | 88 | 80 | | 78 | 80 |
| | D | | 99 | 93 | | 88 | 97 |
| 21 | M | | 91 | 79 | | 74 | 90 |
| | D | | 99 | 90 | | 96 | 94 |
| 22 | M | | 72 | 63 | | 60 | 70 |
| | D | | 98 | 77 | | 99 | 100 |
| 23 | M | | 90 | 55 | | 82 | 71 |
| | D | | 64 | 87 | | 100 | 100 |
| 24 | M | | 91 | 62 | | 86 | 84 |
| | D | | 68 | 97 | | 99 | 100 |
| 25 | M | | 87 | 40 | | 97 | 88 |
| | D | | 88 | 93 | | 100 | 100 |
| 26 | M | | 98 | 75 | | 99 | 93 |
| | D | | 100 | 99 | | 100 | 100 |
| 27 | M | | 76 | 74 | | 82 | 99 |
| | D | | 98 | 90 | | 100 | 100 |
| 28 | M | | 74 | 79 | | 73 | 73 |
| | D | | 95 | 79 | | 99 | 100 |
| 29 | M | | 74 | 66 | | 79 | 97 |
| | D | | 73 | 84 | | 100 | 100 |
| 30 | M | | 81 | 78 | | 75 | 91 |
| | D | | 99 | 94 | | 100 | 100 |
| 31 | M | | 74 | 68 | | 61 | 68 |
| | D | | 99 | 69 | | 100 | 100 |
| 32 | M | | 86 | 81 | | 86 | 100 |
| | D | | 100 | 81 | | 100 | 100 |
| 33 | M | | 53 | 79 | | 32 | 65 |

TABLE II-continued

| | | HERBICIDAL ACTIVITY (% control) | | | | | |
|---|---|---|---|---|---|---|---|
| Compound of | | Preemergence | | | Postemergence | | |
| Example No. | lb./A. | 10 | 4 | 2 | 10 | 4 | 2 |
| | D | | 99 | 74 | | 98 | 100 |
| 34 | M | | 35 | 83 | | 32 | 47 |
| | D | | 52 | 85 | | 89 | 90 |
| 35 | M | | 40 | 60 | | 45 | 63 |
| | D | | 40 | 72 | | 98 | 80 |
| 36 | M | | 93 | 100 | | 87 | 94 |
| | D | | 100 | 100 | | 100 | 98 |
| 37 | M | | 99 | 100 | | 92 | 100 |
| | D | | 100 | 100 | | 100 | 100 |
| 38 | M | | 47 | 62 | | 43 | 51 |
| | D | | 86 | 68 | | 98 | 58 |
| 39 | M | | 65 | 77 | | 64 | 61 |
| | D | | 99 | 80 | | 98 | 100 |
| 40 | M | | 86 | 88 | | 64 | 81 |
| | D | | 92 | 98 | | 100 | 100 |
| 41 | M | | 60 | 84 | | 71 | 56 |
| | D | | 96 | 62 | | 95 | 94 |
| 42 | M | | 62 | 83 | | 38 | 63 |
| | D | | 80 | 60 | | 98 | 88 |
| 43 | M | | 0 | 99 | | 2 | 61 |
| | D | | 48 | 100 | | 47 | 80 |
| 44 | M | | 66 | 0 | | 60 | 7 |
| | D | | 96 | 17 | | 98 | 10 |
| 45 | M | | 13 | 68 | | 17 | 53 |
| | D | | 58 | 77 | | 88 | 78 |
| 46 | M | | 0 | 34 | | 0 | 0 |
| | D | | 20 | 87 | | 30 | 4 |
| 47 | M | | 61 | 80 | | 11 | 24 |
| | D | | 40 | 80 | | 72 | 84 |
| 48 | M | | 99 | 100 | | 75 | 84 |
| | D | | 97 | 100 | | 100 | 97 |
| 49 | M | | 92 | 100 | | 86 | 77 |
| | | | 95 | 100 | | 100 | 100 |
| 50 | M | | 90 | 98 | | 97 | 100 |
| | D | | 83 | 100 | | 100 | 100 |
| 51 | M | | 79 | 96 | | 75 | 86 |
| | D | | 100 | 100 | | 100 | 98 |
| 52 | M | | 79 | 98 | | 87 | 93 |
| | D | | 67 | 75 | | 100 | 100 |
| 53 | M | | 98 | 98 | | 79 | 81 |
| | D | | 83 | 100 | | 100 | 100 |
| 54 | M | | 83 | 98 | | 79 | 71 |
| | D | | 45 | 98 | | 100 | 100 |
| 55 | M | | 91 | | | 69 | 31 |
| | D | | 73 | | | 95 | 96 |
| 56 | M | | 91 | 100 | | 99 | 100 |
| | D | | 83 | 100 | | 100 | 99 |

*M = Monocots: D = Dicots
**¼ lb./A.
+½ lb./A.

EXAMPLE 74

This example shows the selective herbicidal activity of diphenyl ethers of the invention in a number of agronomic crops. Following the general test procedure of Example 73, diphenyl ethers are evaluated for significant tolerance (as shown by 50% or less kill of the test crop at levels of application which give more than 50% kill of many or all of the weeds of Example 73) towards some or all of the following common agronomic crops (not all compounds tested against all crops): alfalfa, snapbeans, corn, cotton, cucumbers, peanuts, rape, rice, safflower, soybeans, tomatoes, and wheat.

Tolerance to snapbeans in preemergence applications is shown by the compounds of Examples 4 and 26. Tolerance to corn in preemergence applications is shown by the compounds of Examples 4, 11, 19, 21, 34, 40, 52, and 54 and in postemergence applications by the compounds of Examples 4, 18, 19, 21, 26, 34, 36, 40, 52, 53, 54, and 56. Tolerance to cotton in preemergence applications is shown by the compounds of Examples 3, 4, and 30 and in postemergence of layby applications by the compound of Example 3. Tolerance to peanuts in preemergence applications is shown by the compounds of Examples 3, 19, 21, 30, 34, 36, 40, 48, 49, 50, 52, 53, and 56 and in postemergence applications by the compounds of Examples 4, 18, 34, 36, 37, 40, 48, 53, and 54. Tolerance to rice in preemergence applications is shown by the compounds of Examples 4, 19, 21, 30, 34, 40, 52, and 54 and in postemergence applications or in applications or transplanted rice by the compounds of Examples 3, 11, 18, 20, 30, 34, 40, 48, 53, and 54. Tolerance to safflower in preemergence applications is shown by the compound of Example 3. Tolerance to soybeans in preemergence applications is shown by the compounds of Examples 3, 4, 11, 18, 19, 21, 26, 30, 34, 40, 48, 49, 50, 52, 53, and 54, in postemergence or layby applications by the compounds of Examples 3 and 34. Tolerance to wheat in preemergence applications is shown by the compounds of Example 4, 18, 19, 26, 34, 40, 50, 54, and 56 and in postemergence applications by the compounds of Examples 4, 18, 21, 30, 34, 36, 48, and 54.

It is to be understood that changes and variations may be made without departing from the spirit and scope of the invention as defined by the appended claims.

We claim:

1. A herbicidal composition comprising a compound of the formula

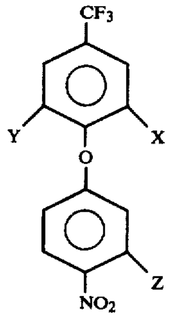

wherein

X is a cyano group,

Y is a hydrogen atom, a halogen atom, or a trifluoromethyl group, and

Z is a hydroxy group, an alkoxy group having up to 6 carbon atoms, an alkyl group having up to 4 carbon atoms, a halogen atom, an amino group, an alkylthio group having up to 4 carbon atoms, a cyano group, a carboxyalkyl group having up to 4 carbon atoms, or an agronomically-acceptable salt thereof, a carbalkoxyalkyl group having up to 6 carbon atoms, an alkanoyloxy group having up to 4 carbon atoms, or a carbamoyloxy group having up to 6 carbon atoms, and an agronomically-acceptable carrier.

2. A composition according to claim 1 wherein the carrier is an inert organic solvent.

3. A composition according to claim 2 which also comprises a surfactant.

4. A method of controlling weeds which comprises applying to the surface of the growth medium prior to the emergence of the weeds from the growth medium a compound of the formula

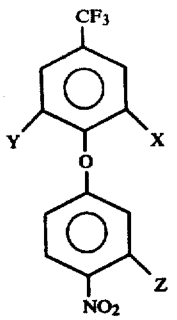

wherein

X is a cyano group,

Y is a hydrogen atom, a halogen atom, or a trifluoromethyl group, and

Z is a hydroxy group, an alkoxy group having up to 6 carbon atoms, an alkyl group having up to 4 carbon atoms, a halogen atom, an amino group, an alkylthio group having up to 4 carbon atoms, a cyano group, a carbalkoxyalkyl group having up to 4 carbon atoms, or an agronomically-acceptable salt thereof, a carbalkoxyalkyl group having up to 6 carbon atoms, an alkanoyloxy group having up to 4 carbon atoms, or a carbamoyloxy group having up to 6 carbon atoms, in an amount sufficient to control the growth of the weeds.

5. The method of claim 4 wherein the compound is applied at a rate of about 0.1 to about 12 pounds per acre.

6. A method of controlling weeds which comprises applying to weed seedlings a compound of the formula

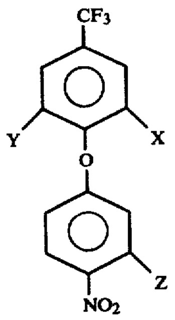

wherein

X is a cyano group,

Y is a hydrogen atom, a halogen atom, or a trifluoromethyl group, and

Z is a hydroxy group, an alkoxy group having up to 6 carbon atoms, an alkyl group having up to 4 carbon atoms, a halogen atom, an amino group, an alkylthio group having up to 4 carbon atoms, a cyano group, a carboxyalkyl group having up to 4 carbon atoms, or an agronomically-acceptable salt thereof, a carbalkoxyalkyl group having up to 6 carbon atoms, an alkanoyloxy group having up to 4 carbon atoms, or a carbamoyloxy group having up to 6 carbon atoms in an amount sufficient to control the growth of the seedlings.

7. The method of claim 6 wherein the compound is applied at a rate of about 0.1 to about 12 pounds per acre.

8. A method of controlling undesirable plant growth which comprises applying to the area in which growth is to be controlled a growth controlling amount of the herbicidal composition of claim 1.

9. A method of selectively controlling weeds in an agronomic crop which comprises applying to or incorporating into the growth medium prior to planting the crop and prior to the emergence of the weeds from the growth medium a compound of the formula

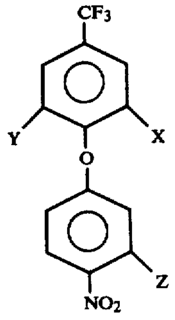

wherein

X is a cyano group,

Y is a hydrogen atom, a halogen atom, or a trifluoromethyl group, and

Z is a hydroxy group, an alkoxy group having up to 6 carbon atoms, an alkyl group having up to 4 carbon atoms, a halogen atom, an amino group, an alkylthio group having up to 4 carbon atoms, a cyano group, a carboxyalkyl group having up to 4 carbon atoms, or an agronomically-acceptable salt thereof, a carbalkoxyalkyl group having up to 6 carbon atoms, an alkanoyloxy group having up to 4 carbon atoms, or a carbamoyloxy group having up to 6 carbon atoms in an amount sufficient to control selectively the growth of the weeds.

10. The method of claim 9 wherein the compound is applied or incorporated at a rate of about 0.1 to about 12 pounds per acre.

11. A method of selectively controlling weeds in an agronomic crop which comprises applying to weed seedlings a compound of the formula

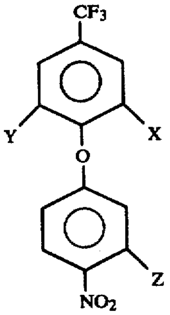

wherein

X is a cyano group,

Y is a hydrogen atom, a halogen atom, or a trifluoromethyl group, and

Z is a hydroxy group, an alkoxy group having up to 6 carbon atoms, an alkyl group having up to 4 carbon atoms, a halogen atom, an amino group, an alkylthio group having up to 4 carbon atoms, a cyano group, a carboxyalkyl group having up to 4 carbon atoms, or an agronomically-acceptable salt thereof, a carbalkoxyalkyl group having up to 6 carbon atoms, an alkanoyloxy group having up to 4 carbon atoms, or a carbamoyloxy group having up to 6 carbon atoms in an amount sufficient to control selectively the growth of the weeds.

12. The method of claim 11 wherein the compound is applied at a rate of about 0.1 to about 12 pounds per acre.

* * * * *